United States Patent
Göhler et al.

(10) Patent No.: US 7,123,024 B2
(45) Date of Patent: Oct. 17, 2006

(54) DEVICE COMPRISING A MICROWAVE RESONATOR FOR OR ON A SPINNER PREPARATION MACHINE

(75) Inventors: Wolfgang Göhler, Lenting (DE); Chokri Cherif, Ingolstadt (DE)

(73) Assignee: Rieter Ingolstadt Spinnereimaschinenbau AG, Ingolstadt (DE)

( * ) Notice: Subject to any disclaimer, the term of this patent is extended or adjusted under 35 U.S.C. 154(b) by 0 days.

(21) Appl. No.: 10/545,106

(22) PCT Filed: Feb. 13, 2004

(86) PCT No.: PCT/EP2004/001351

§ 371 (c)(1),
(2), (4) Date: Aug. 10, 2005

(87) PCT Pub. No.: WO2004/072337

PCT Pub. Date: Aug. 26, 2004

(65) Prior Publication Data

US 2006/0071670 A1    Apr. 6, 2006

(30) Foreign Application Priority Data

Feb. 13, 2003  (DE) ............................... 103 06 209

(51) Int. Cl.
  *G01R 27/04* (2006.01)
  *G01R 27/32* (2006.01)
  *D01H 5/32* (2006.01)
(52) U.S. Cl. .................... 324/634; 324/635; 19/239
(58) Field of Classification Search ............. 324/633, 324/634–637, 629, 600, 639, 640, 643, 644, 324/664, 689; 19/236, 239, 23; 73/73, 433
See application file for complete search history.

(56) References Cited

U.S. PATENT DOCUMENTS

| 5,103,180 A | 4/1992 | Lahitte et al. |
| 5,397,993 A | 3/1995 | Tews et al. |
| 5,845,529 A * | 12/1998 | Moshe et al. ............. 73/73 |

(Continued)

FOREIGN PATENT DOCUMENTS

EP    0564359 B1    10/1993

(Continued)

OTHER PUBLICATIONS

German Search Report, filed Dec. 23, 2003.

(Continued)

*Primary Examiner*—Anjan Deb
*Assistant Examiner*—Hoai-An D. Nguyen
(74) *Attorney, Agent, or Firm*—Dority & Manning

(57) ABSTRACT

A device is disclosed, comprising a microwave resonator, for or on a spinner preparation machine with drawing gear (2) for drawing fiber material (FB), in particular a carding, drawing or combing machine, whereby the resonator (30) is embodied for connection to a measuring device (16) for measuring the strip density (mass per unit length) or the strip thickness and/or the dampness of the fiber material (FB), continuously passing through the resonator chamber (31). Said device is characterized in that the resonator (30) is integrated in a functional group (20; 120; 220; 320; 420) of the spinner preparation machine which is typical for the machine. A spinner preparation machine, in particular a carding, drawing or combing machine, is further disclosed which comprises a corresponding device.

29 Claims, 4 Drawing Sheets

U.S. PATENT DOCUMENTS

Figures 1, 1A, 1B:
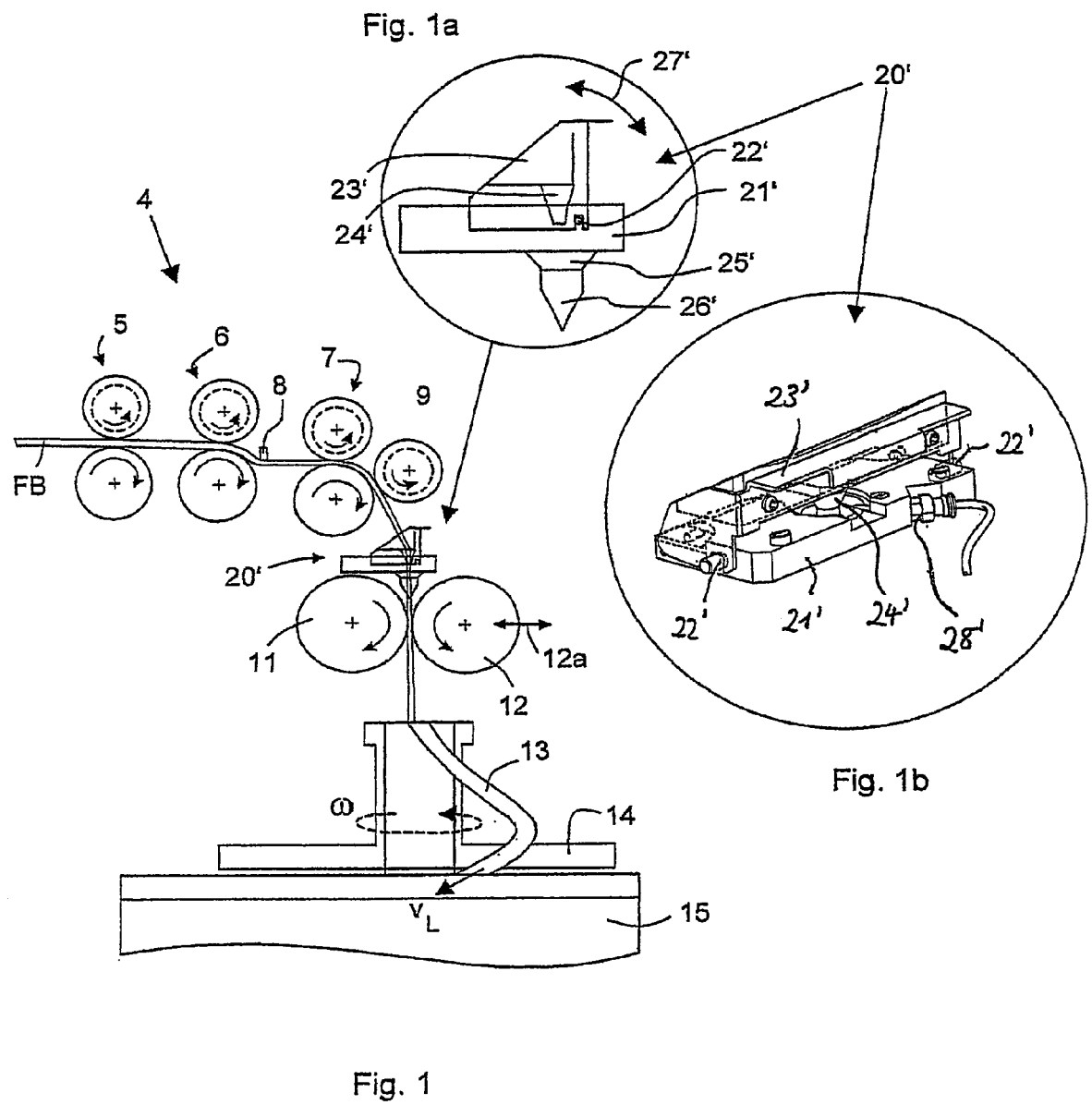

| | | | |
|---|---|---|---|
| 5,990,767 A | 11/1999 | Ivanov et al. | |
| 6,025,724 A * | 2/2000 | Moshe et al. | 324/640 |
| 6,417,676 B1 | 7/2002 | Schröder et al. | |
| 6,476,619 B1 * | 11/2002 | Moshe et al. | 324/634 |
| 6,837,122 B1 | 1/2005 | Herrmann et al. | |
| 6,874,204 B1 * | 4/2005 | Dammig et al. | 19/236 |
| 6,880,207 B1 * | 4/2005 | Cherif et al. | 19/238 |
| 6,983,516 B1 * | 1/2006 | Dammig et al. | 19/239 |
| 2003/0150266 A1 * | 8/2003 | Dammig et la. | 73/433 |

FOREIGN PATENT DOCUMENTS

EP    1325683 B1    7/2003

OTHER PUBLICATIONS

International Preliminary Examination Report, filed Sep. 16, 2005.

* cited by examiner

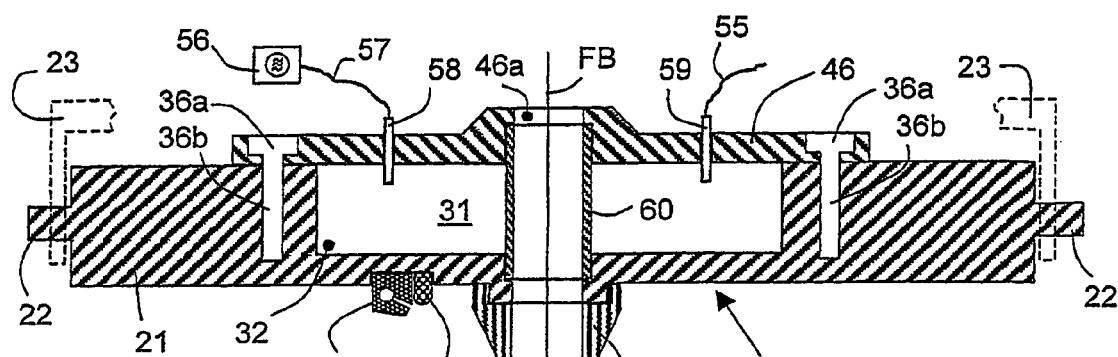
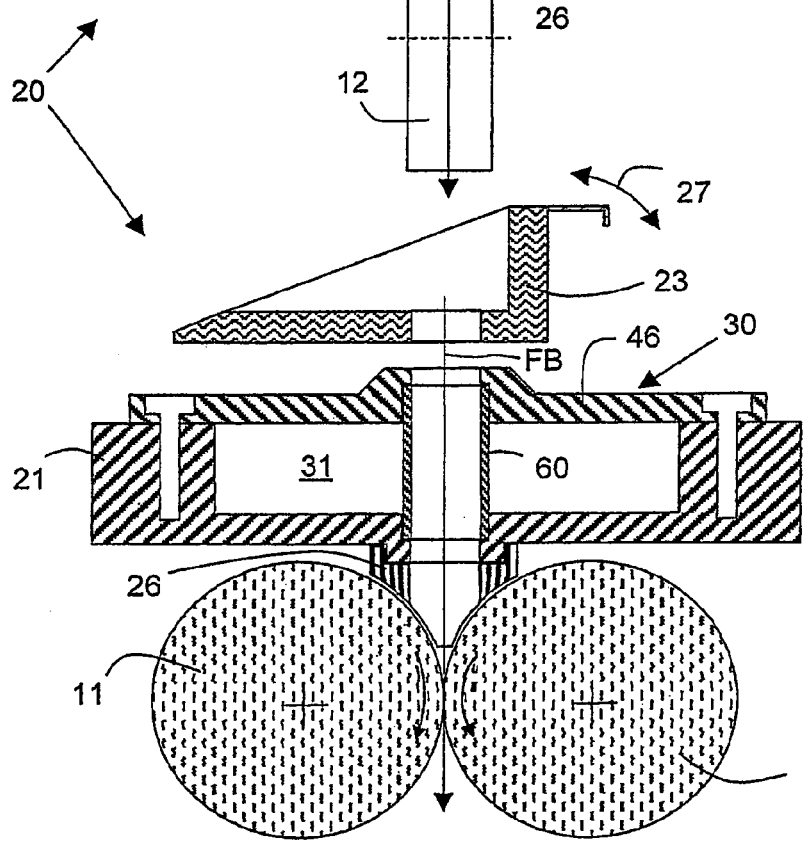
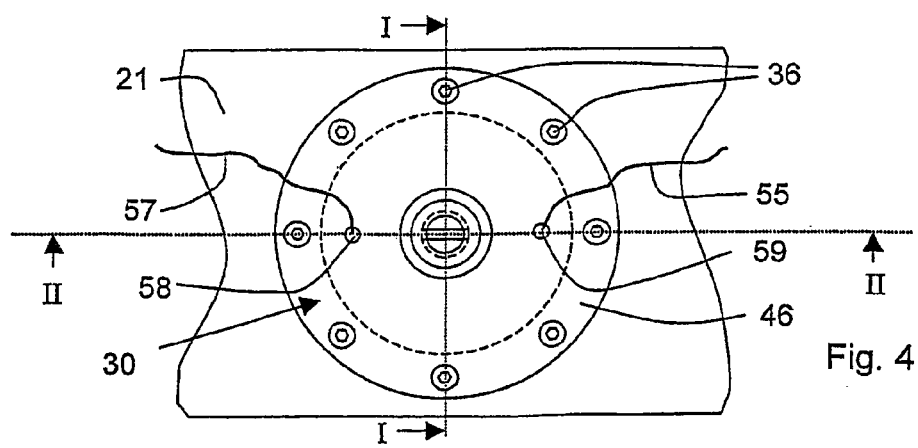

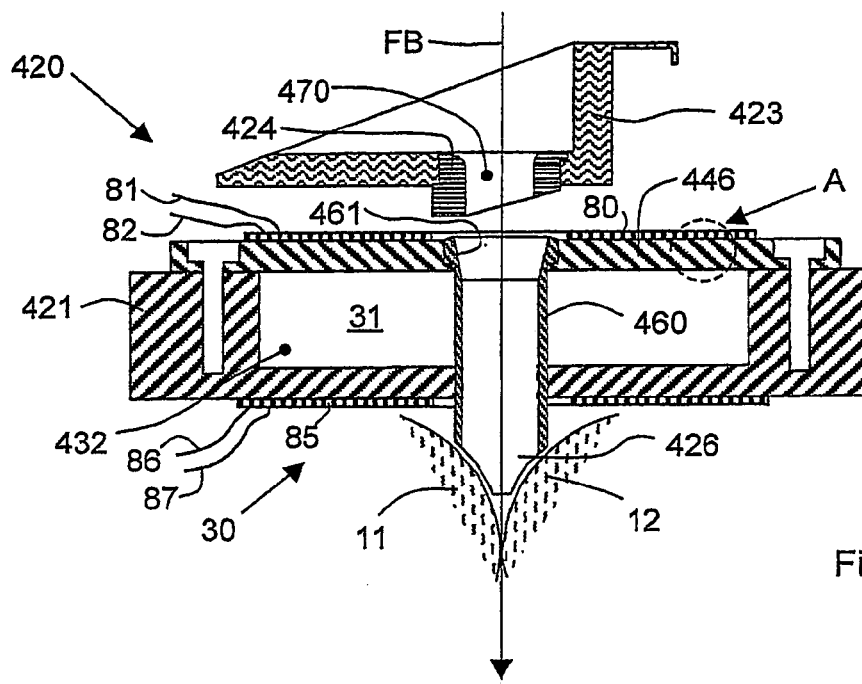
Fig. 8
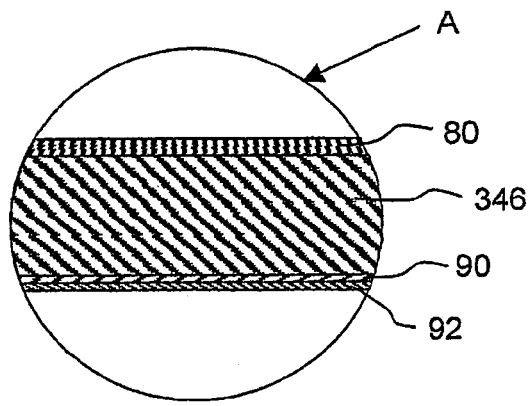
Fig. 9
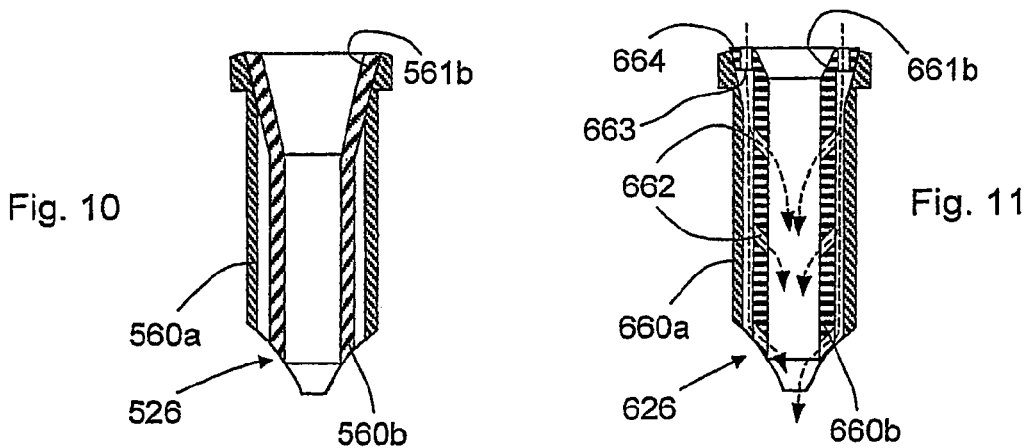
Fig. 10
Fig. 11

DEVICE COMPRISING A MICROWAVE RESONATOR FOR OR ON A SPINNER PREPARATION MACHINE

The invention relates to a device with a microwave resonator for or on a spinning mill preparation machine having drafting equipment for the drawing of skein-shaped fiber material, in particular a carding, drawing or combing machine, whereby the resonator is designed for connection to a measuring device to measure sliver density or sliver thickness and/or the moisture of the fiber material continuously conveyed through the resonator chamber.

The measuring of fiber sliver thickness is essential especially for the purpose of regulating irregularities of one or several fiber slivers presented to a spinning mill preparation machine. Measuring of this type at the output of the machine is also desirable for quality control of the drawn material. Measured values regarding fiber sliver density or fiber sliver thickness also commonly called sliver cross-section or sliver mass; in case of microwave measurement the terms sliver density, i.e. of the sliver mass per unit of length is generally used are used in addition to the above-mentioned quality control also to stop the machine if limit values for mass fluctuation is exceeded so that no high-quality product can any longer be obtained.

In the past mainly mechanically scanning sensors were used to determine sliver thickness of the fiber sliver or slivers. Capacitive measuring elements are also known. Now the utilization of microwave represents a new method for the measuring of fiber sliver density or thickness. With this method microwaves produced by a microwave generator having a frequencies that are preferably modified by a computer within certain limits are coupled into a resonator chamber of a microwave resonator through which the fiber material to be measured is also conveyed continuously. Depending on the type of fiber, the sliver masses and sliver geometry as well as on sliver moisture, a resonance signal occurs at a characteristic microwave frequency which can be evaluated after uncoupling by a computer to determine the sliver density mass per unit of length or the sliver thickness and/or the sliver moisture of the fiber material. Such a method used in other applications is described e.g. in EP 0468023 B1, the disclosures of which are explicitly included herewith. The advantages of such a measuring method by means of microwaves consist in particular in the fact that highly precise, contact-free scanning of the fiber material is possible. Mechanical damage to the sliver as well as lack of measuring precision due to inertia of mechanical measuring elements is eliminated.

For the layout of a microwave resonator it appears obvious that it should be positioned where normally the mechanically scanning sensors are located. For example, at the output of a drafting equipment the mechanical sensor is as a rule part of a pair of calender rollers used to convey the drawn fiber sliver. One of the two calender rollers is here designed so that it can be moved against a pressure force, whereby the extent of the movement is a measure for the sliver thickness of the fiber sliver running through. Since the pair of calender rollers serves however in particular to convey the fiber sliver out of the drafting equipment, the latter cannot be omitted, so that finding space for the microwave sensor presents a problem.

It is the object of the present invention to realize a simple positioning of a microwave resonator, especially where space is limited.

This object is attained in a device of the type mentioned initially in that the resonator is integrated into a machine-typical functional group of the spinning mill preparation machine. The object is also attained by a spinning mill preparation machine with such a device.

The advantages of the invention consist in particular in the fact that the resonator is not installed in empty spaces that may be available but that a known function group is modified in order to integrate the resonator mechanically therein. The resonator thus becomes part of the functional group. Thereby space can be saved on the hand, and on the other hand a highly functional unit is obtained that can last but not least also be designed so as to be easily accessible. Since a great variety of functional elements that must also be easily accessible e.g. for maintenance and cleaning can be provided in the known functional group, this advantage is also accrued for the microwave resonator. The microwave resonator is thus combined with a functional group of the textile machine so that this combination serves several functions at the same time.

The functional group with the microwave resonator is most preferably installed at the drafting equipment output. In conventional machines the space between the last drafting rollers and the pairs of calender or draw-off rollers is extremely limited. In order to avoid major rebuilding of the existing machines, the distance between the aforementioned drafting roller and the pair of draw-off rollers is preferably left unchanged. The functional group in this interval comprises in particular a supporting structure on which the elements for sliver monitoring, sliver guidance and/or sliver threading are installed. In the known draw frame RSB-D 35 of the Rieter company a fibrous-web guiding nozzle is connected in particular at such a supporting structures and is swiveled away by the piled-up sliver in case of sliver pile-up above the supporting structure thus causing a switching off of the machine. Furthermore a holding device is used in a central opening of the supporting structure in which again a sliver funnel is introduced. The sliver funnel serves to compact the fiber material brought together by the fibrous-web guiding nozzle and to effect a precise introduction into the nip of the downstream pair of calender rollers. In the known draw frame RSB-D 35 two air channels are furthermore provided through which a stream of compressed air is conveyed in order to convey a fiber sliver end threaded into the fibrous-web guiding nozzle by means of the air stream through the sliver funnel to the calender rollers.

According to the invention one or several of the above-mentioned elements are now present also in those supporting structures into which the microwave resonator is integrated. The above-mentioned elements for sliver monitoring, sliver guidance and/or sliver threading can also have a configuration that is different from the previously described one.

Preferably a sliver pile-up sensor is also installed at the supporting structure between the drafting equipment and the draw-off equipment and serves in particular to register a sliver pile-up between a sliver funnel located at the supporting structure and the draw-off equipment, i.e. in particular a pair of calender rollers. Such a sensor can be based on an optical measuring principle, on mechanical registration or some other measuring principle.

The resonator chamber is preferably cylindrical and also larger in the direction of the perpendicular to the fiber sliver than in the direction of fiber sliver movement. Since the space between drafting equipment and draw-off equipment is limited in known machines, as mentioned earlier, such a design is advantageous. In particular the coupling and uncoupling elements which couple and uncouple the microwaves in the resonator chamber can find room more easily with this design and can be connected by means of connection elements.

The connections for coupling and uncoupling the microwaves in the resonator chamber are preferably arranged so as to be adapted to the applicable conditions or requirements. Thus it may be advantageous to place the connections on the side of fiber material arrival, since easy access is facilitated here for servicing on the one hand, since a sliver pile-up at the calender rollers does not damage the connections. With connections located laterally on the other hand, an even smaller and flatter component can be achieved.

The microwave resonator can either be an autonomous part of the functional group or the functional group and at least part of the resonator can be made in one piece. In the latter case it is advantageous if the resonator chamber is formed at least in part by an indentation in the functional group. It may, for example, consist of a ground-out recess. To cover the resonator chamber a removable wall element is preferably placed on the depression and may be screwed on, for example. The wall element can be flush with the surface of the functional group or may protrude, for example. If a supporting structure is provided as part of the functional group at the drafting equipment output, the latter then serves not only to receive a holding device for a sliver funnel and to attach a fibrous-web guidance nozzle as well as in some cases other elements for sliver monitoring, sliver guidance and/or sliver threading, but is itself part of a microwave sensor.

In an alternative embodiment the functional group has an opening on which a first or second wall element is installed from one and the other side. The resonator chamber is then formed between the two wall elements. This embodiment has the advantage, among others, that the two wall element can be designed so as to be easily removable e.g. to allow for cleaning tasks. It is then also possible to replace the wall elements easily and inexpensively in case of damage or wear.

In a special embodiment the two wall element constitute on the one hand the covering wall and on the other hand the bottom wall of the resonator chamber, while its surrounding lateral wall is constituted by the functional group. Alternatively the lateral walls of the resonator chamber are also formed by a segment of one or two wall elements.

To convey the fiber material through the resonator chamber, the functional group and one wall element or two wall element have passage openings aligned with each other. An electrically non-conductive pipe open at both ends is preferably inserted into these passage openings so that the sliver material can be conveyed through it. Textile fibers can thus not enter the remaining portion of the resonator chamber so that cleaning that would otherwise be necessary from time to time can be omitted.

The guide pipe is preferably made of an essentially temperature-stable material whose relative permittivity is furthermore essentially independent of temperature. It is possible to use ceramic, a compound material or synthetic material for this, in the latter case in particular polycarbonate. Furthermore the microwave measurements should as much as possible not be influenced. Furthermore it is advantageous if the material used accepts as little moisture as possible. As a compound material TMM® of the American Rogers company has proven to be especially good, consisting of a hydrocarbon/ceramic compound material with very good temperature stability and especially a very stable relative permittivity with respect to temperature fluctuations.

In a preferred variant embodiment the guide pipe is conical or funnel-shaped in the direction of fiber sliver movement, at least in part, in order to already compact the fiber material to some degree for a downstream pair of calender rollers.

To simplify the threading of the fiber material into the resonator, the input opening of the guide pipe can be widened and can in particular be conical.

Since the guide pipe is designed preferably so that it can be exchanged, a suitable guide pipe with modified inside diameter can be selected for each sliver thickness. The evaluation of the uncoupled microwave signals is advantageously coordinated with the currently used guide pipe. Such a new adjustment of the evaluation software may be unnecessary if the dimensions of the different guide pipes are selected so as to be substantially of equal size within the area of microwave dispersion. This requires a correspondingly suitable geometry selection for the pipes.

The preceding embodiment concerns the case that only one pipe goes through the resonator chamber in each instance, i.e. that the outside diameter of the different pipes remains the same with different inside diameters. In alternative embodiments at least two guide pipes are provided, whereby one inside pipe is installed, e.g. inserted into an outside pipe. The fiber material is then conveyed in the inside pipe while the outside guide pipe does not necessarily come in contact with the fiber material. In that case different inside guide pipes with different inside diameters can also be inserted at different times into the outside pipe which has preferably the same diameter. The outside pipe serves mainly as support on the supporting co0nstruction and to receive the inside pipe. The precision of the resonance signal evaluation with the different inside pipes can be ensured in this embodiment also by new adjustment of the evaluation software and/or by identical mass of the inside pipe within the microwave dispersion range.

In a further development of the idea of having at least two pipes with one inserted into the other, the outside pipe can have a continuous pipe surface while the inside pipe has openings, e.g. one or several holes. In this manner e.g. compressed air can be introduced into the interval between the two pipe walls, entering through the hole or holes and serving as a threading assistance and/or conveying assistance for the fiber sliver to be conveyed through the resonator chamber. When the fiber sliver is absent, the inside pipe can also be cleaned in this manner.

In principle t is advantageous to provide a blowing or suction device at the resonator in order to convey the fiber sliver or slivers through the resonator chamber and to keep it clean.

The guide pipe is preferably connected or can be connected at its downstream side to a sliver funnel so that this unit can assume a double function with minimal space requirement. In a direct connection with each other, the sliver funnel can e.g. be slipped over the pipe end, can be screwed to it or be connected to it in some other manner. Alternatively it is also possible to make the guide pipe and the sliver funnel in one piece. The sliver funnel presents the drawn fiber sliver preferably to a nip of a downstream pair of calender rollers so that the free distance traveled by the fiber sliver between the sliver funnel and the pair of calender rollers is as short as possible.

In an alternative embodiment the sliver funnel can be installed on the supporting structure or on a removable wall element without any connection to the guide pipe.

Since it has been shown that heat expansion of the resonator walls may result in false measurements, care should preferably be taken to ensure substantially constant temperature conditions. One possibility consists in making the functional group in the resonator area heatable, and for this purpose e.g. a heating foil heated with electric voltage can be applied to the functional group in order to rapidly reach a desired, constant temperature. Such a foil can be located advantageously at the underside and/or on the top of the resonator chamber. In the embodiment of the resonator chamber as described above, using one or several wall elements, these too can be heated. The regulation of the temperature level may be ensured e.g. by the microwave electronics, by a central machine control or by a dedicated regulation. When the desired temperature is reached or shortly before, the electric circuit is opened while it is again closed when the temperature falls below a predetermined limit value.

Instead of heating, the elements of the device can also be cooled to a constant temperature, e.g. by means of Peltier elements.

Alternatively or in addition, materials with low heat expansion are used for the functional group or at least for the resonator. An advantageous design is here the utilization of steel with preferably high nickel content, in particular Ni 36 steel. Invar® steel is for example steel of that type, having a very low heat expansion coefficient.

Alternatively or in addition thermally insulated materials are used on the functional group in order to ensure a constant temperature level. In a special embodiment thermally insulated material is integrated into the functional group. If the resonator is made as a separate part of the functional group for example, and is installed in a corresponding opening in the functional group or supporting structure, thermally insulated material can be provided at the contact points in order to minimize the heat transmission from the adjoining segment of the functional group which is generally made of steel to the resonator.

Alternatively or in addition the resonator together with the functional group can be installed in a thermally insulated housing. Passages for the fiber material must of course be provided.

When using materials with low thermal expansion such as e.g. steel with preferably high nickel content, the expansion capability of the microwave field in the resonator may suffer. Accordingly a preferred embodiment of the invention consists in that the resonator chamber is provided with a conductive coating on its inside wall, consisting e.g. of a low-oxygen copper coating.

In order to prevent corrosion of the inside surfaces of the resonator chamber, it may be advantageous to apply a corrosion-proof coating consisting e.g. of gold or silver. This is especially advantageous if the previously mentioned conductive coating e.g. of copper is used. In that case the corrosion of the copper is prevented by the application of a gold or silver coating.

Alternatively or in addition, the resonator chamber is filled in a gastight manner with a gas protecting from corrosion which in particular may not contain any oxygen for that purpose. The utilization of inert gas is recommended in particular for this.

In addition to the described device, a spinning mill preparation machine, in particular a carding machine, draw frame or combing machine with the device according to the invention is part of the present invention. The previously described guide pipe for replaceable installation of the above-described device in a microwave resonator is also part of the invention.

Advantageous further developments of the invention are characterized by the characteristics of the sub-claims.

The invention is described in further detail below through the figures.

Figure 5:
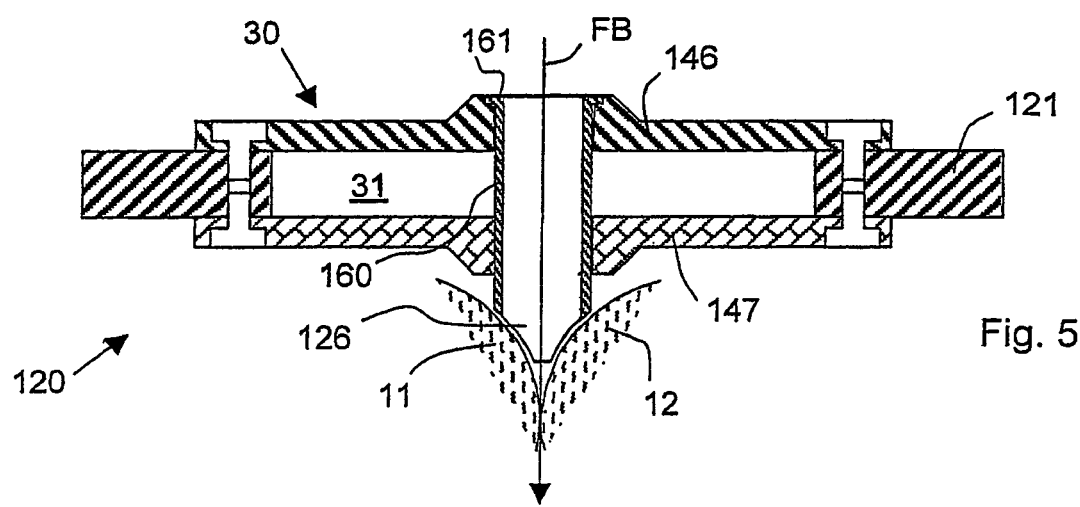
Figure 6:
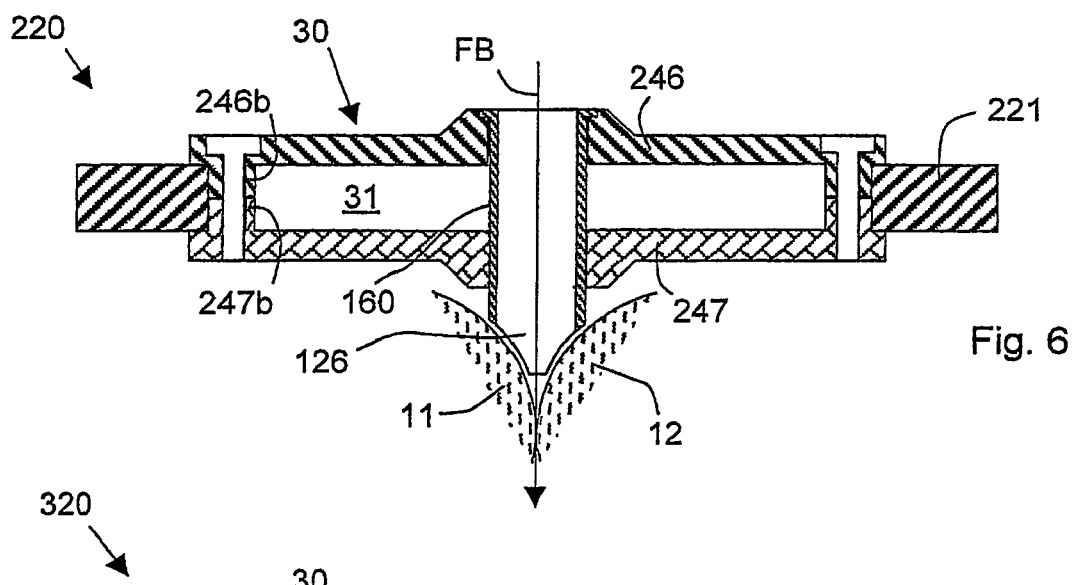
Figure 7:
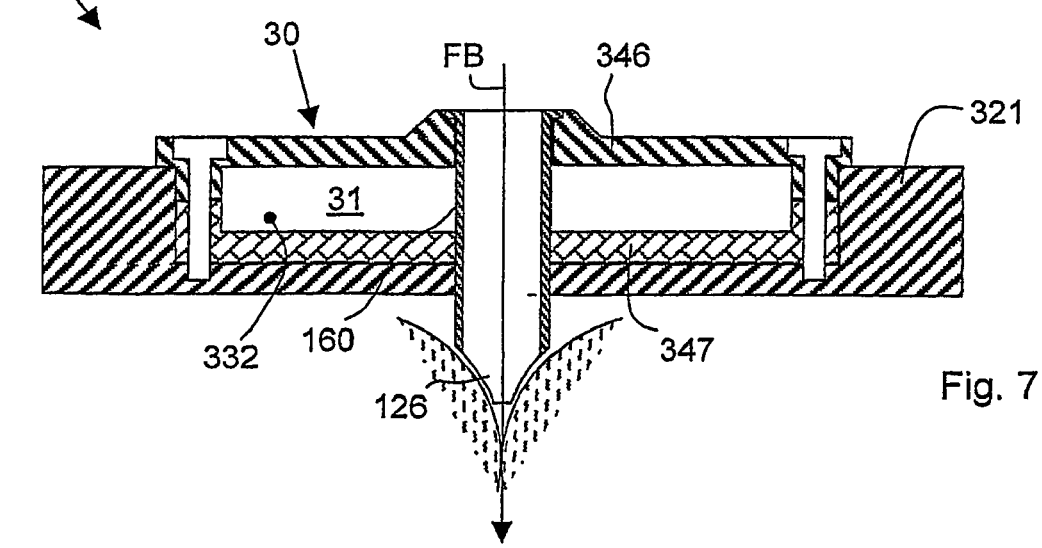

FIG. 1 shows a schematic lateral view of a draw frame according to the state of the art, FIG. 1a, 1b shows a functional group between the drafting equipment output and calender rollers in an enlarged view in lateral and perspective views, FIG. 2 shows a functional group according to the invention with a microwave resonator in a sectional frontal view cut along II—II in FIG. 4, FIG. 3 shows the functional group as in FIG. 2 in a sectional lateral view cut along I—I in FIG. 4, FIG. 4 shows a top view of the functional group according to FIGS. 2 and 3 at a smaller scale, FIG. 5 shows a sectional lateral view of a functional group according to a second embodiment, FIG. 6 shows a sectional lateral view of a functional group according to a third embodiment, FIG. 7 shows a sectional lateral view of a functional group according to a fourth embodiment, FIG. 8 shows a sectional lateral view of a functional group according to a fifth embodiment with two heating foils, FIG. 9 shows a detail from FIG. 8;

FIG. 10 shows a sectional detailed view of a special embodiment of two pipes pushed inserted into each other in form of dielectric insulator and FIG. 11 shows a sectional detail view of another embodiment of two pipes inserted into each other.

In FIG. 1 the essential elements of a known draw frame are shown. The heart of such a draw frame is the drafting equipment 4 which is provided in the embodiment shown with a pair of input rollers 5, a central pair of rollers 6 and a pair of output or delivery rollers 7 rotating in that sequence at respectively increased circumferential speeds. One or several fiber slivers FB are clamped between the different rollers of the roller pairs 5, 6, 7 and are drafted in function of the ratio of circumferential speeds of the roller pairs. In the main drafting field which is formed by the central pair of rollers 6 and the delivery rollers 7 a pressure rod 8 is provided in addition for the deflection of the fiber sliver FB. The drafted fiber sliver or slivers FB are gathered together into several sliver guiding elements see FIGS. 1a, 1b b means of an upper deflection roller 9 and are introduced via a pair of calender rollers 11, 12 into a curved sliver channel 13. The sliver channel 13 is located in a rotating plate 14 rotating at an angular speed ω causing the fiber sliver FB to be deposited at a speed $V_L$ in a rotating or traversing can 15. The calender roller 12 in this known draw frame is movable and powered see double arrow 12a whereby the extent of the excursion is a measure of the sliver cross-section of the fiber sliver FB running between the pair of calender rollers 11, 12. The signals regarding the excursion are transmitted to an evaluation unit not shown here which serves to compute the fiber sliver quality. The machine can be stopped automatically if limit values of the sliver cross-section are exceeded or not reached.

FIGS. 1a and 1b show the sliver guiding elements of the known functional group 20' between the drafting equipment 4 and the pair of calender rollers 11, 12 in enlarged drawings. The schematically shown embodiment according to FIG. 1a corresponds to that of the known draw frame RSB D30 of the Rieter Company. The plate-shaped supporting structure 21' is here the central element. The supporting structure 21' is provided with lateral bearing bolts 22' for the coupling of a swiveling fibrous-web guiding nozzle 23' (also called a fibrous-web funnel) so that the latter can be swiveled forward (see double arrow 27') in case of sliver pile-up at the nozzle 23'. This fibrous-web guiding nozzle 23' forms the fibrous-web or fiber sliver FB coming out of the drafting equipment 4 into a more solid sliver. A fibrous-web nozzle insert 24' through which the fiber sliver FB is guided is inserted in this fibrous-web guiding nozzle 23'. In the direction of sliver movement, a holder 25' held in the supporting structure flows, and in it a sliver funnel 26' with a beak-shaped end segment is inserted into it in downstream direction.

In FIG. 1*b* it can furthermore be seen that a compressed-air connection 28' is provided at the supporting structure 21' to facilitate the threading of a fiber sliver end into the fibrous-web guiding nozzle 23', the fibrous-web nozzle insert 24' and the sliver funnel 26'.

FIGS. 2 and 3 show a first embodiment of the invention in frontal view and lateral view, each in central cutaway. A functional group 20 comprises a plate-shaped supporting structure 21 at which, on two opposing sides, as also in the state of the art, contact bolts 22 are provided for the installation of a fibrous-web guiding nozzle 23 that can be swiveled in the direction of double arrow 27 (see FIG. 3, not shown in FIGS. 2 and 4). The supporting structure 21 has a central indentation 32 which is cylindrical in the embodiment shown (see also FIG. 4). An optical sensor 50 located in a shallow recess is on the underside of the supporting structure 21, whereby the sensor surface is kept free from fiber fly by means of a cleaning device 51 emitting compressed air.

In addition a sliver funnel 26 essentially in form of a hollow beak is installed in the area of a passage opening at the underside of the supporting structure 21 and is attached e.g. by means of a screw connection not shown in detail in a detachable manner to the supporting structure 21. Different fastening possibilities for the sliver funnel 26 are also possible: thus for example, an additional holder can be provided between the sliver funnel 26 and the supporting structure 21.

A wall element 46 is set on the indentation 32 and in the shown embodiment is in form of a flat cylinder disk with screw holes 36*a* on its borders that are aligned with corresponding blind bores 36*b* in the supporting structure 21. As in FIG. 4 in which they are shown at a smaller scale than in FIGS. 2 and 3, hexagonal-head screws 36 can be screwed into these bores 36*a*, 36*b* each of which is provided with inside threads in order to screw the wall element 46 to the supporting structure 21 (the screws are not shown in FIGS. 2 and 3). In an alternative not shown here the wall element 46 can be fitted and screwed into a recess in the supporting structure 21 in a plane parallel to the top of the supporting structure 21.

The wall element 46 set on the indentation 32 constitutes a resonator chamber 31 of a microwave resonator 30 into which microwaves are coupled by means of a coupling element 58 and from which they can be uncoupled by means of an uncoupling element 59. Both coupling elements 58, 59 extend through suitable bores in the wall element 46 from the outside into the resonator chamber 31. The coupling element 58 is connected via a cable 57 to a schematically indicated microwave generator 56 whose frequency can be varied by means of a control unit (preferably a microprocessor) not shown here. The uncoupling element 59 is in turn connected via a cable 55 to an evaluation unit not shown here. The uncoupling element 59 receives the microwave signals formed in the resonator and transmits them to the evaluation unit so that through the latter the applicable resonance frequency and appertaining signal width can be ascertained at sequential points in time. From this information the sliver thickness or sliver mass per unit of length of the fiber material currently running through the resonator chamber can be ascertained.

Set into the indentation 32 is a guide pipe 60 made of dielectric material which rests at its two faces in corresponding step-shaped receptacles in the supporting structure 21 or in the wall element 46. The passage opening in the guide pipe 60 is aligned with the central passage openings in the wall element 46, in the supporting structure 21 and in the sliver funnels 26. The fiber sliver FB (indicated only schematically as an arrow) can thus be conveyed in a linear manner through the functional group 20 directly into the gap between the two calender rollers 11, 12 (see in particular FIG. 3).

The guide pipe 60 is easily replaced by unscrewing and removing the wall element 46. Depending on the type of material and drafting conditions, different inserts 60 can be used.

An additional sliver guiding element not shown here can be provided between the fibrous-web guiding nozzle 23 and the wall element 46, similar to the fibrous-web guiding nozzle insert 24 of the state of the art of FIG. 1.

FIGS. 5 to 8 show additional embodiments of the invention in sectional lateral views. The calender rollers 11, 12 are only indicated therein.

In the embodiment of a functional group 120 according to FIG. 5 the resonator chamber 31 is covered on one side by a wall element 146 and on the other side by a wall element 147. The wall elements 146, 1457 constitute in this case the top and the bottom of the resonator chamber 31 while the surrounding lateral wall is constituted by the supporting structure 121. The wall elements 146, 147 are connected to the supporting structure 121 by means of screws (here again, only the corresponding bores with inside threads are shown). Instead of two screws across from each other it is of course also possible in a variant that is not shown to introduce screws merely from one side to end in corresponding blind bores in the other wall element.

The supporting structure 121 can be continuous and surround the resonator 30 from all sides when seen from above (similarly to the embodiment shown in FIG. 4). In a variant which is not shown the supporting structure 121 is however made in two parts, whereby the two parts are connected to each other via the wall elements 146, 147, again as seen from above. The wall elements 146, 147 constitute in that case a kind of bridge in which the resonator 30 is located.

In the embodiment of a functional group 220 of FIG. 6, two wall elements 246, 247 alone, i.e. without participation by inside surfaces of the supporting structure 221, constitute the resonator chamber 31. For this purpose the two wall elements 246, 247 are provided with circumferential beads 246*b*, 247*b* facing each other, in which bores aligned with each other are provided for the introduction of screws (not shown). The resonator 30 can, as described earlier in connection with the embodiment according to FIG. 5, be imbedded in a one-piece supporting structure 221, or the wall elements 246, 247 can connect two or more parts of a divided supporting structure 221.

The fourth embodiment of a functional group 320 shown in FIG. 7 is characterized by the fact that a wall element 347 is set into a depression 332 in the supporting structure 321 and in that an additional wall element 346 is placed on this wall element 347 and is screwed to it by means of screws (not shown). In this embodiment the resonator chamber 31 is also surrounded merely by the two wall elements 346, 347. The supporting structure 321 can be made of a suitable metal, as in the case of FIG. 221, or of a metal alloy or a synthetic material. In the latter case the synthetic material can have a thermally insulating effect.

The embodiments shown in FIGS. 5 to 7 show a guide pipe 160 with which a sliver funnel 126 with a downstream beak-shaped end segment is made in one piece and lays the fiber sliver FB between the calender rollers 11, 12 which are only indicated in the cutout. The guide pipe 160 has a circumferential bead at its end away from the pair of calender rollers 11, 12 which pressed against a correspondingly stepped border of the passage opening of the upper wall element 146, 246 or 346. In this manner a secure support of the guide pipe 160 is ensured in the microwave resonator 30 on the one hand while on the other hand the guide pipe 160 can be replaced quickly and easily.

In other embodiments not shown in particular, the supporting structure 21, 121, 221, 321 can be designed in such manner that the wall elements 146, 147, 246, 247, 346 are flush with the supporting structure 21, 121, 221, 321.

FIG. 8 shows an embodiment of a functional group 420 which is similar to that of FIGS. 2 to 4 see FIG. 3 in particular. Again a removable wall, element 446 covers a depression 432 and is screwed to a supporting structure 421 by means of screws that are not shown. On a side of the wall element 446 away from the microwave resonator 30 a first electrical heating foil 80 is attached, while on the opposite side of the supporting structure 421 a second heating foil 85 is attached on the outside. The two heating foils 80, 85 are connected via connection wires 81, 82 and 86, 87 to a heat source that is not shown. The heat capacity is advantageously adjusted, in this case e.g. to 35° C. For this purpose one or more temperature measuring devices which are not shown are provided, e.g. reaching into one or several lateral bores in the supporting structure 421 near the resonator chamber 31. A thermal insulation sleeve which may e.g. surround the entire supporting structure, with suitable openings for the fiber material, can also be provided to prevent the influence of temperature fluctuations in the surroundings as well as to prevent heat capacity loss.

Other additional or alternative measures for the stabilization of the temperature may consist in that elements surrounding the resonator chamber 31 are made in all shown embodiments of a material with little heat expansion, e.g. Invar® steel. In addition other elements of the entire functional group can be made of such a material. According to the enlarged detail A of FIG. 9, the inside wall of the microwave resonator 30 in the embodiment of FIG. 8 is provided with a conductive coating 90, e.g. of low-oxygen copper, since the Invar® steel of the wall element 446 and of the supporting structure 421 is only minimally conductive. Microwave resonances with sufficient signal strength may not be generated without such a conductive coating. To prevent corrosion of the coating 90, a corrosion-proof coating 92 e.g. of gold or silver is in addition applied on it. Alternatively, a ceramic material or a compound with imbedded ceramic can be used as coating or covering.

A guide pipe 460 is placed in the resonator chamber 31 of FIG. 8 and is provided with a conical widening 461 in the vicinity of the wall element 446. The opposite face is in form of a sliver funnel 426 see also FIGS. 5 to 7 which present the fiber sliver FB as close as possible in the nip between the calender rollers 11, 12.

Above the wall element 446 a fibrous-web guiding nozzle 423 is provided see also FIG. 3 with a bore 470 into which a fibrous-web nozzle insert is inserted and held by means of a centering pin that is not shown. On the side away from the guide pipe 460 the fibrous-web nozzle insert 24 is rounded off circumferentially in order to ensure a gentle introduction of the fiber sliver FB into the guide pipe 460.

In each of the FIGS. 10 and 11 an inside guide pipe 560*b* or 660*b* each with conical widening 561*b* or 661*b* is inserted into an outer pipe 560*a* or 660*a*, whereby each combination can be inserted e.g. into a microwave resonator 30 as shown in FIG. 8. At each of the undersides of the outer guide pipes 560*a* or 660*a* a sliver funnel 526 or 626 is installed but could also be installed on the inside guide pipes 560*b* or 660*b*. These two embodiments have the advantage that the outer pipe 560*a* or 660*a* can remain inserted in the resonator while the inside pipe 560*b* or 660*b* can be replaced with one having a smaller or greater inside diameter. In this manner the applicable sliver characteristics e.g. narrower or wider sliver diameter; type of textile material, etc. can be taken into account. It is advantageous in that case if the masses of the different inside guide pipes 560*b* or 660*b* are essentially of equal size in the area of the microwave dispersion, so that no new calibration of the microwave resonator 30 is necessary when replacing the inside pipes 560*b* or 660*b*.

In the embodiment of FIG. 11 the outer pipe 660*a* as well as the pipe 560*a* of FIG. 10 has a continuous pipe wall while the inside pipe 660*b* has openings 662 in form of several holes distributed over the circumference and at intervals in longitudinal direction. Also on the upper bead 664 which is circular as seen from above, openings 663 are provided through which blown or compressed air can be introduced from a compressed-air source which is not shown into the space between the inside wall of the outer pipe 660*a* and the outer wall of the inside pipe 660*b* into the interior of pipe 660*b* see broken-line arrows and can serve there to thread the fiber sliver and/or to convey it through the resonator. Alternatively or in addition the compressed air can be used to clean the above-mentioned intermediate space between the two pipes as well as the interior of the inside pipe 660*b*.

The pipes shown in the examples of embodiments are preferably made of an essentially temperature-stable material with a relative permittivity that is furthermore essentially non-dependent on temperature. Ceramic material or synthetic material, e.g. polycarbonate can be used here.

The invention which is described in greater detail by means of the figures is not limited to these embodiments. The resonator chamber in particular can use different geometries other than a cylindrical form. Furthermore the guide pipe can also be made with sliver guiding elements other or in addition to the sliver funnel, e.g. in form of a fibrous web forming element upstream of the resonator chamber. The device according to the invention can also be placed before the drafting equipment, whereby the functional group that is typical for the machine also has elements for sliver monitoring, sliver guidance and/or sliver threading for the mechanical integration of the resonator. In a card-draw frame combination a device according to the invention can for example be provided at the input as well as at the output of the draw frame. The invention can be used with regulated as well as with unregulated draw frames, cards and combing machines.

The invention claimed is:

1. A spinning mill preparation machine having drafting equipment for drawing fiber sliver material, said machine comprising:

a functional group element associated with said drafting equipment that performs a typical drafting function, said functional group element further comprising a support structure with at least one fiber sliver guidance, monitoring, or threading device attached thereto; and a sliver measuring device, for measuring at least one of the sliver density, the sliver thickness or the moisture of the fiber sliver, including a microwave resonance chamber through which the sliver fiber material is conveyed, said resonance chamber defined within said support structure of said functional group element such that space in addition to that occupied by said support structure is not required within said machine to accommodate said resonance chamber.

2. The spinning mill preparation machine as in claim 1, wherein said functional group element is located at an output of said drafting equipment.

3. The spinning mill preparation machine as in claim 1, wherein said resonance chamber comprises a cylindrical shape having a larger dimension perpendicular to a running direction of the sliver through said resonance chamber as compared to a dimension parallel to the running direction of the sliver.

4. The spinning mill preparation machine as in claim 3, further comprising at least one connection on an upstream wall of said cylindrical resonance chamber with respect to the running direction of the sliver for microwave coupling and uncoupling devices.

5. The spinning mill preparation machine as in claim 3, further comprising at least one connection on a downstream wall of said cylindrical resonance chamber with respect to the running direction of the sliver for microwave coupling and uncoupling devices.

6. The spinning mill preparation machine as in claim 3, further comprising connections on a lateral wall of said cylindrical resonance chamber for microwave coupling and uncoupling devices.

7. The spinning mill preparation machine as in claim 1, wherein said resonance chamber is defined at least in part by a recess or depression in said support structure of said functional group element.

8. The spinning mill preparation machine as in claim 7, further comprising a removable wall element attached to said functional group element over said recess or depression.

9. The spinning mill preparation machine as in claim 1, wherein said resonance chamber is defined at least in part by a removable wall element attached to said functional group element.

10. The spinning mill preparation machine as in claim 1, wherein said resonance chamber is defined by an opening through said support structure of said functional group element, and further comprising wall elements attached at opposite ends of said opening to define end walls of said resonance chamber.

11. The spinning mill preparation machine as in claim 1, further comprising an opening through said support structure of said functional group element and wall elements attached at opposite ends of said opening, said wall elements defining opposite end walls of said resonance chamber and further comprising circumferential beads that extend into said opening to define lateral walls of said resonance chamber.

12. The spinning mill preparation machine as in claim 1, further comprising an electrically non-conductive guide pipe within said resonance chamber through which the fiber sliver material is conveyed.

13. The spinning mill preparation machine as in claim 12, wherein said guide pipe is conical over at least a portion thereof.

14. The spinning mill preparation machine as in claim 12, wherein said guide pipe comprises a conical sliver input opening.

15. The spinning mill preparation machine as in claim 12, further comprising a sliver funnel disposed at a downstream end of said guide pipe.

16. The spinning mill preparation machine as in claim 15, wherein said sliver funnel and said guide pipe are made as a single piece.

17. The spinning mill preparation machine as in claim 12, wherein said guide pipe is removable and replaceable with a different said guide pipe having a different inside diameter and the same outside diameter.

18. The spinning mill preparation machine as in claim 17, wherein said different guide pipe has generally the same mass as the initial said guide pipe.

19. The spinning mill preparation machine as in claim 12, wherein said guide pipe comprises an outer pipe element concentric with an inner pipe element, the fiber sliver material conveyed through said inner pipe element.

20. The spinning mill preparation machine as in claim 19, wherein said inner pipe element is removable from said outer pipe element and replaceable with a different inner pipe element having a different inside diameter.

21. The spinning mill preparation machine as in claim 19, wherein a space between said inner and outer pipe elements is in communication with a compressed air source, said inner pipe element comprising openings through which compressed air is introduced into said inner pipe element.

22. The spinning mill preparation machine as in claim 1, further comprising at least one heating foil attached to said functional group element at a location so as to maintain a generally constant temperature within said resonance chamber.

23. The spinning mill preparation machine as in claim 1, further comprising thermal insulating material attached to said functional group element at a location so as to maintain a generally constant temperature within said resonance chamber.

24. The spinning mill preparation machine as in claim 1, wherein components of said functional group element defining said resonance chamber are formed of material having a low heat expansion coefficient.

25. The spinning mill preparation machine as in claim 24, wherein said material comprises a nickel-steel material.

26. The spinning mill preparation machine as in claim 1, further comprising a low oxygen copper conductive coating within said resonance chamber.

27. The spinning mill preparation machine as in claim 26, further comprising a corrosion proof coating applied over said conductive coating.

28. The spinning mill preparation machine as in claim 1, wherein said resonance chamber is filled with an inert gas.

29. The spinning mill preparation machine as in claim 1, wherein said machine is one of a card machine, draw frame, or combing machine.

* * * * *